(12) United States Patent
Margaria et al.

(10) Patent No.: US 12,064,528 B2
(45) Date of Patent: Aug. 20, 2024

(54) SYSTEMS, METHODS, AND DEVICES FOR MICROBIAL DECONTAMINATION ON SCOOTERS

(71) Applicant: Ford Global Technologies, LLC, Dearborn, MI (US)

(72) Inventors: Gilles Margaria, Lauro de Freitas (BR); Rodrigo Denizarte de Oliveira Polkowski, Camacari (BR); Julio Okada, Salvador (BR); Eduardo Pinto, Camacari (BR); Cristiano Grings Herbert, Salvador (BR); Alper Kiziltas, Sarikamis (TR); Deborah Frances Mielewski, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 691 days.

(21) Appl. No.: 17/317,774

(22) Filed: May 11, 2021

(65) Prior Publication Data

US 2022/0362425 A1  Nov. 17, 2022

(51) Int. Cl.
*A61L 2/24* (2006.01)
*A61L 2/04* (2006.01)
(Continued)

(52) U.S. Cl.
CPC .............. *A61L 2/24* (2013.01); *A61L 2/04* (2013.01); *B62K 3/002* (2013.01); *B62K 21/26* (2013.01);
(Continued)

(58) Field of Classification Search
CPC .......... A61L 2/04; A61L 2/24; A61L 2202/16; B62K 3/002; B62K 21/26
See application file for complete search history.

(56) References Cited

U.S. PATENT DOCUMENTS 6,844,524 B2   1/2005   Downey et al.
6,903,312 B2   6/2005   Miura et al.
(Continued)

FOREIGN PATENT DOCUMENTS

CN          109018106 A      12/2018

OTHER PUBLICATIONS

Amazon.co.uk website link to purchase: 'Motorcycle Grip Handlebar Electric Heating Hand Cover Heating Handle, Winter Motorcycle Riding Adjustable Temperature discloses a handlebar heating system that allows a user to adjust the temperature of the handlebars,' (3 pages).

*Primary Examiner* — Thien S Tran
(74) *Attorney, Agent, or Firm* — Emily Drake; Eversheds Sutherland (US) LLP

(57) ABSTRACT

Devices, systems, and methods for controlling microbial contamination of scooters are disclosed. A method may include determining that a user interaction with a vehicle is complete, presenting a first indication that the vehicle is unavailable for use, activating a heating element of the vehicle, the heating element associated with a microbial reduction process, determining that a time period associated with the microbial reduction process has expired, deactivating, based on the expiration of the time period, the heating element of the vehicle, and presenting a second indication that the vehicle is available for use.

20 Claims, 5 Drawing Sheets

(51) Int. Cl.
 B62K 3/00 (2006.01)
 B62K 21/26 (2006.01)
(52) U.S. Cl.
 CPC ....... *A61L 2202/14* (2013.01); *A61L 2202/16* (2013.01); *A61L 2202/20* (2013.01)

(56) References Cited

U.S. PATENT DOCUMENTS

| | | |
|---|---|---|
| 6,984,807 B2 | 1/2006 | Richlen |
| 7,291,814 B2 | 11/2007 | Oishi et al. |
| 2017/0327172 A1* | 11/2017 | Osanai ................... B60R 16/037 |
| 2019/0058982 A1* | 2/2019 | Lee ......................... B62K 19/40 |
| 2019/0202383 A1* | 7/2019 | Odate ..................... B60R 16/03 |
| 2023/0218793 A1* | 7/2023 | Spillner ................... A61L 2/18 |
| | | 15/302 |

* cited by examiner

SYSTEMS, METHODS, AND DEVICES FOR MICROBIAL DECONTAMINATION ON SCOOTERS

BACKGROUND

People increasingly are using motor vehicles, such as scooters, for transportation and recreation. In particular, multiple people may use the same scooter. As a result of multiple users of a scooter, germs may be present on the scooter for a certain period of time and may contaminate the next riders.

BRIEF DESCRIPTION OF THE DRAWINGS

The detailed description is set forth regarding the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
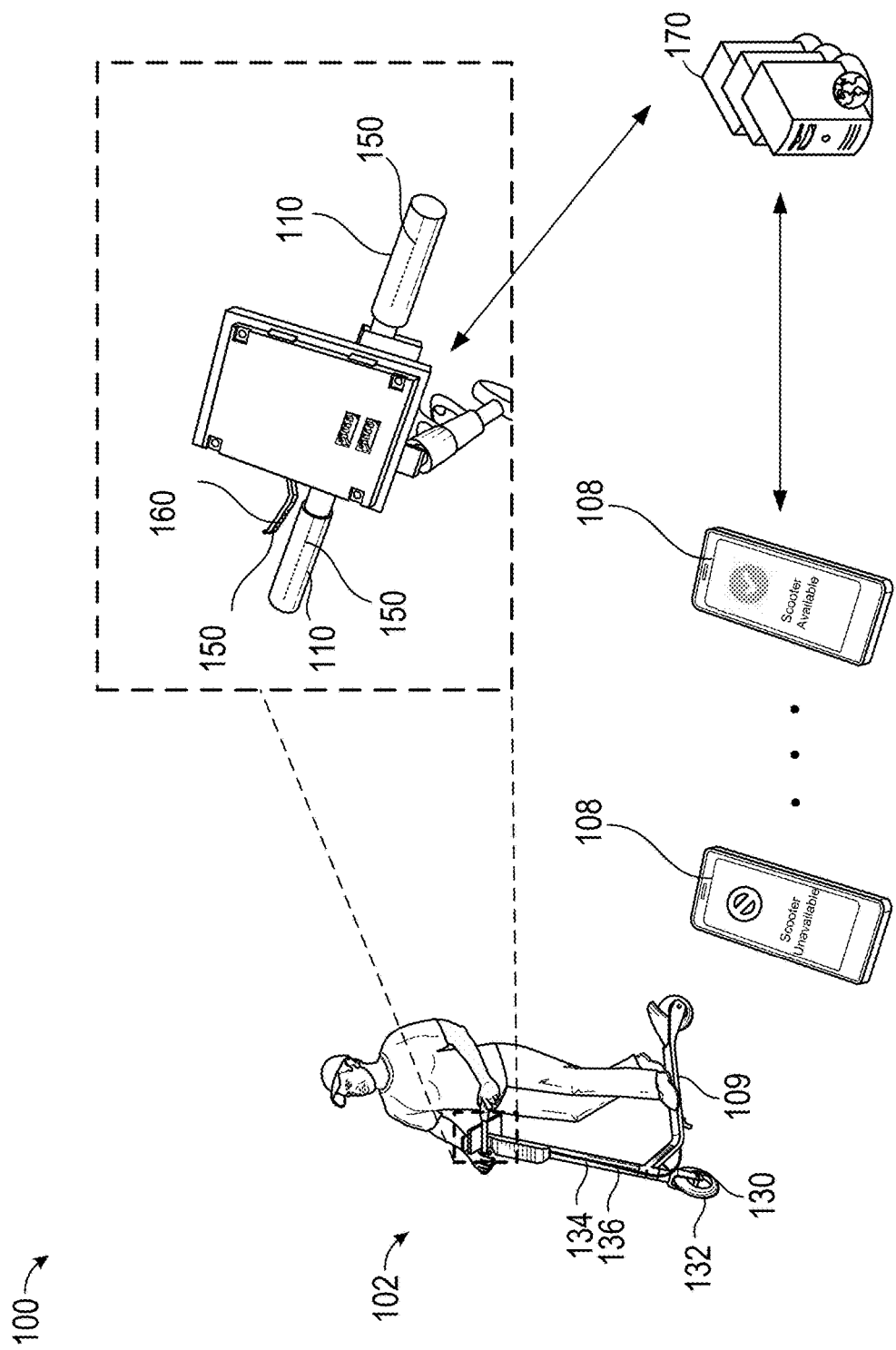
FIG. 1 depicts an illustrative scooter system in which techniques and structures for providing the systems and methods disclosed herein may be implemented.

People may use scooter sharing and other motor vehicle sharing services that result in multiple people using the same scooter or motor vehicle at different times. When one person rides a scooter after another person has ridden the scooter, the scooter may have microbial microorganisms that may be undesirable and potentially harmful to the next rider (e.g., when a previous rider was ill). The transmission of pathogenic viruses and bacteria that can cause diseases, such as but not limited to some respiratory disorders, asthma, influenza, covid19, and those diseases may occur through the contact with surfaces since microbial microorganisms may stay alive for a such period of time on surfaces such as but not limited to plastic, rubber, steel.

Some existing scooters, snowmobiles, and other motor vehicles, may have warming mechanisms, such as heated handlebars, to improve a user's experience. However, high temperatures needed to eliminate microbial microorganisms may not be suitable for or desirable to users when riding a scooter. In addition, eliminating microbial microorganisms may require an application of heat for a period of time without a user touching or breathing on the scooter.

Therefore, it may be desirable to control the times at which scooters apply heat to its components, and to prevent usage while the heat is being applied.

In one or more embodiments, a scooter or other device may include one or more heating elements. For example, a scooter may have handlebars with one or more heating elements. The heating elements may be activated when a rider is not using the scooter, and use of the scooter may be prevented until the heating elements have been deactivated. The heating elements may be used to eliminate microbial microorganisms, and may use temperatures of 56 degrees Celsius or higher for periods of time lasting at least 15 minutes.

In one or more embodiments, a user device (e.g., a smartphone or other device) using an application may allow a user to reserve a scooter for use. When a user finishes using the scooter, the application may provide an indication that the use of the scooter is complete, and the scooter may activate the one or more heating elements to perform decontamination. The scooter may activate one or more locking mechanisms or otherwise may not activate during the decontamination. When a user attempts to reserve and use the scooter during decontamination, the user may be presented with an indication of the decontamination process (e.g., that the user may not use the scooter). The indication may be presented using a display of the scooter and/or using the user device. When the decontamination process is complete, the scooter may deactivate the one or more heating elements, remove any indications that the scooter is unavailable, and may deactivate any locking mechanisms. In this manner, the decontamination process using the heating elements may be activated when the scooter is not in use by a rider, and may prevent subsequent use by another rider until the decontamination process has completed and the heating elements are deactivated.

ILLUSTRATIVE EMBODIMENTS

Turning now to the drawings, FIG. 1 depicts an illustrative scooter system 100 in which techniques and structures of the present disclosure may be implemented. The scooter system 100 can comprise a personal transportation device 102, such as an electronic scooter. The personal transportation device 102 may communicate wirelessly or wired with one or more devices, such as a mobile device 108. The personal transportation device 102 can include a main battery 109 that powers wheels of the personal transportation device 102 through a control mechanism such as handlebars 110.

The personal transportation device 102 may include a power generator 130 in a wheel 132, used to charge batteries 134 housed by a steering column 136. The batteries 134 may power heating elements 150 of the handlebars 110 for the decontamination process.

In one or more embodiments, the mobile device 108 (e.g., a smartphone or other device) using an application may allow a user to reserve the personal transportation device 102 for use. When a user finishes using the personal transportation device 102, the application may provide an indication that the use of the personal transportation device 102 is complete, and the personal transportation device 102 may activate the one or more heating elements 150 (e.g., by providing power from the batteries 134) to perform decontamination. The personal transportation device 102 may activate one or more locking mechanisms or otherwise may not activate during the decontamination (e.g., not providing power from the main battery 109 to the wheels). When a user attempts to reserve and use the scooter during decontamination, the user may be presented with an indication of the decontamination process (e.g., that the user may not use the personal transportation device 102). The indication may be presented using a display of the personal transportation device 102 and/or using the mobile device 108. In some instances, the indication may include a blinking light red light, an audible warning, or a combination thereof. When the decontamination process is complete, the personal transportation device 102 may deactivate the one or more heating elements 150, remove any indications that the personal transportation device 102 is unavailable, and may deactivate any locking mechanisms (e.g., reactivate power from the main battery 109). In this manner, the decontamination process using the heating elements 150 may be activated when the personal transportation device 102 is not in use by a rider, and may prevent subsequent use by another rider until the decontamination process has completed and the heating elements 150 are deactivated.

In one or more embodiments, the time period during which the personal transportation device 102 is deactivated during the decontamination process may depend on the temperature of the heating elements 150. For example, a higher temperature may result in a shorter time period, or a shorter time period may require a higher temperature.

In one or more embodiments, the heating elements 150 may include electrical heating elements may include conductive wires (e.g., silver, copper, gold, nickel, etc.) spanning and/or wound around the handlebars 110 and/or break lever 160 (e.g., that when pulled/squeezed results in deceleration of the personal transportation device 102). In this manner, the handlebars 110 and/or break lever 160 may include dielectric sheath materials or other sleeves to cover the heating elements 150. Alternatively or in addition, the heating elements 150 may include processing circuitry capable of activating conductive elements to heat the handlebars 110 and/or the brake lever 160. For example, the heating elements 150 may use Internet of Things (IoT) technology to communicate with sensors (e.g., as shown in FIG. 2).

In one or more embodiments, the personal transportation device 102 and/or the mobile device 108 may communicate with one or more remote devices 170 (e.g., cloud-based servers or other remote devices). For example, the mobile device 108 may reserve the personal transportation device 102 for a rider's use (e.g., using a mobile application of the mobile device 108). The one or more remote devices 170 may send messages to the personal transportation device 102 indicating whether the personal transportation device 102 has been reserved for use, in which case the personal transportation device 102 may avoid activating the heating elements 150. The personal transportation device 102 may indicate to the one or more remote devices 170 when the personal transportation device 102 has activated and deactivated the heating elements 150, and the one or more remote devices 170 may provide indications to the mobile device 108 when the personal transportation device 102 is available or unavailable (e.g., due to the activation and deactivation of the heating elements 150). The one or more remote devices 170 may provide indications to the mobile device 108 of nearby available transportation devices and/or when a transportation device is unavailable or in decontamination (e.g., to prevent a person from touching the transportation device).

Figure 2:
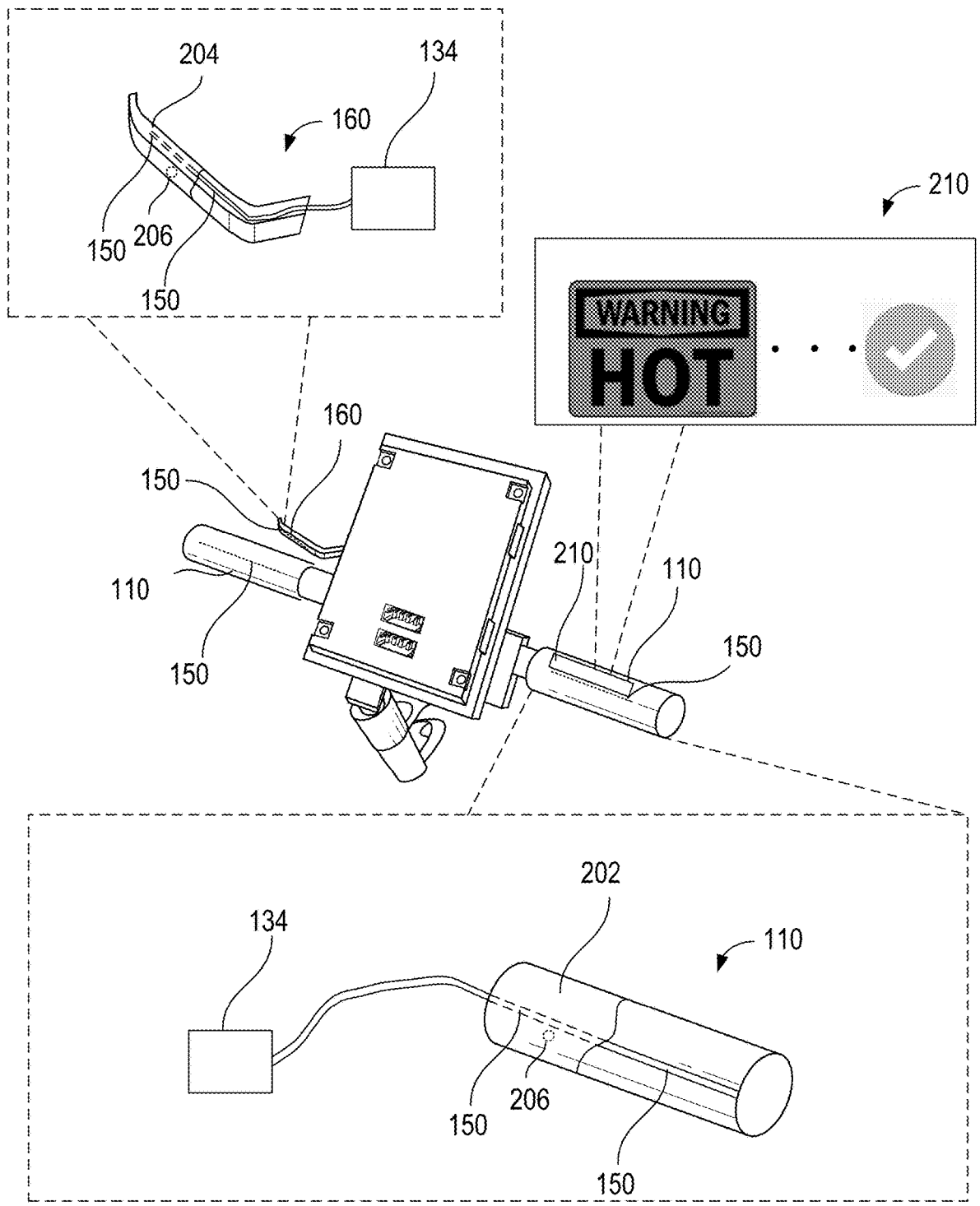
FIG. 2 depicts an illustrative scooter architecture.

FIG. 2 depicts an illustrative scooter architecture 200.

Referring to FIG. 2, the handlebars 110 and the brake lever 160 of the transportation device 102 of FIG. 1 are shown in more detail. As shown in FIG. 2, the handlebars 110 may be at least partially covered with a layer 202 (e.g., shown as partially cut-away) that at least partially covers the heating elements 150 (e.g., so that a user's hands do not come in contact with the heating elements 150). The layer 202 may serve as a sleeve disposed over the handlebars 110 and the heating elements 150, and may be an electrically insulating material such as nylon, rubber, or the like. As shown, the heating elements 150 may extend laterally along the handlebars 110, or as not shown, may wind spirally around the handlebars 110. Similarly, the heating elements 150 may extend laterally or wind spirally around the brake lever 160, with a layer 204 serving as a sleeve, disposed over the handlebars 110 and the heating elements 150 (e.g., similar to the layer 202). The heating elements 150 may include wires extending and connecting electrically to the batteries 134 (e.g., housed by the steering column 136 of FIG. 1), which may provide power to the heating elements 150 when the decontamination process has been activated. The handlebars 110 may include a display 210 (e.g., a digital display) for displaying indications that the transportation device 102 is available, unavailable, in the decontamination process, hot, etc. In this manner, even when the transportation device 102 is unavailable, to prevent anyone from touching a hot surface, the display 210 may indicate that decontamination is occurring (e.g., that the handlebars 110 are hot).

Figure 5:
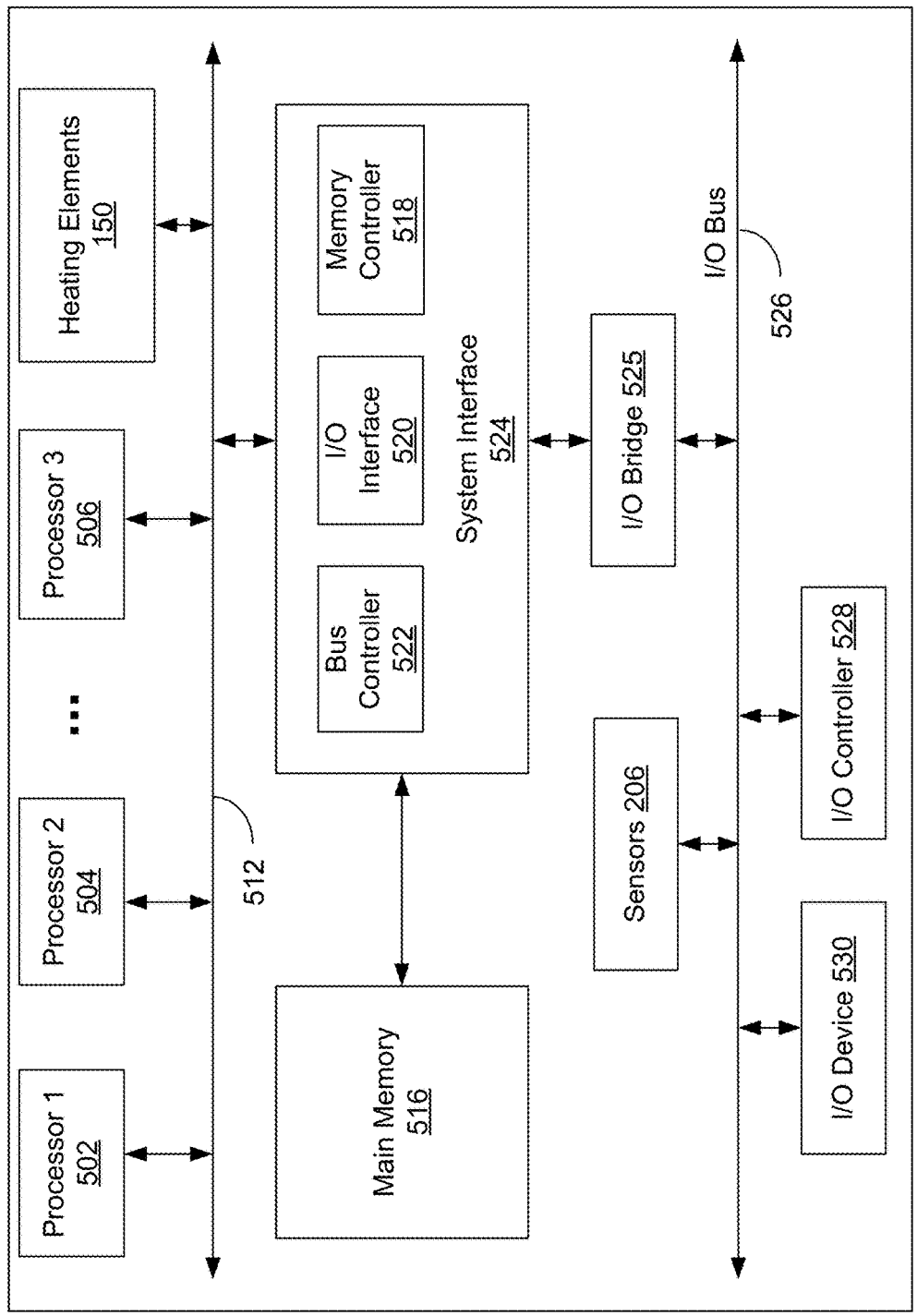
FIG. 5 is a block diagram illustrating an example of a computing device or computer system upon which any of one or more techniques (e.g., methods) may be performed, in accordance with one or more example embodiments of the present disclosure.

In one or more embodiments, the heating elements may include conductive materials that operate as heating wire. The handlebars 110 and the brake lever 160 may include one or more sensors 206 (e.g., temperature and/or pressure sensors) to detect the temperature of the heating elements 150 and/or the pressure applied to the handlebars 110. The heating elements 150 may have or be associated with processing circuitry (e.g., as shown in FIG. 5) to measure temperature and/or pressure, and to activate and deactivate the decontamination process accordingly. For example, when the decontamination process is inactive, a temperature of the handlebars 110 and/or the brake lever 160 exceeding a temperature threshold and/or a pressure applied to the handlebars 110 and/or the brake lever 160 exceeding a pressure threshold may be indicative of contact with a human hand (e.g., use of the transportation device 102). The decontamination process may remain inactive until the temperature and/or pressure are below the temperature or pressure threshold, respectively, for a period of time. The decontamination process may be activated (e.g., resulting in power supplied to the heating elements 150 by the batteries 134) when the temperature and/or pressure are below the temperature or pressure threshold, respectively, for a period of time, and/or when the mobile device 108 of FIG. 1 receives an indication that a user's interaction (e.g., ride session) with the transportation device 102 is complete. The heating elements 150 may use IoT capabilities to communicate with the one or more sensors 206, activating and deactivating based on sensor data detected by the one or more sensors 206.

Figure 3:
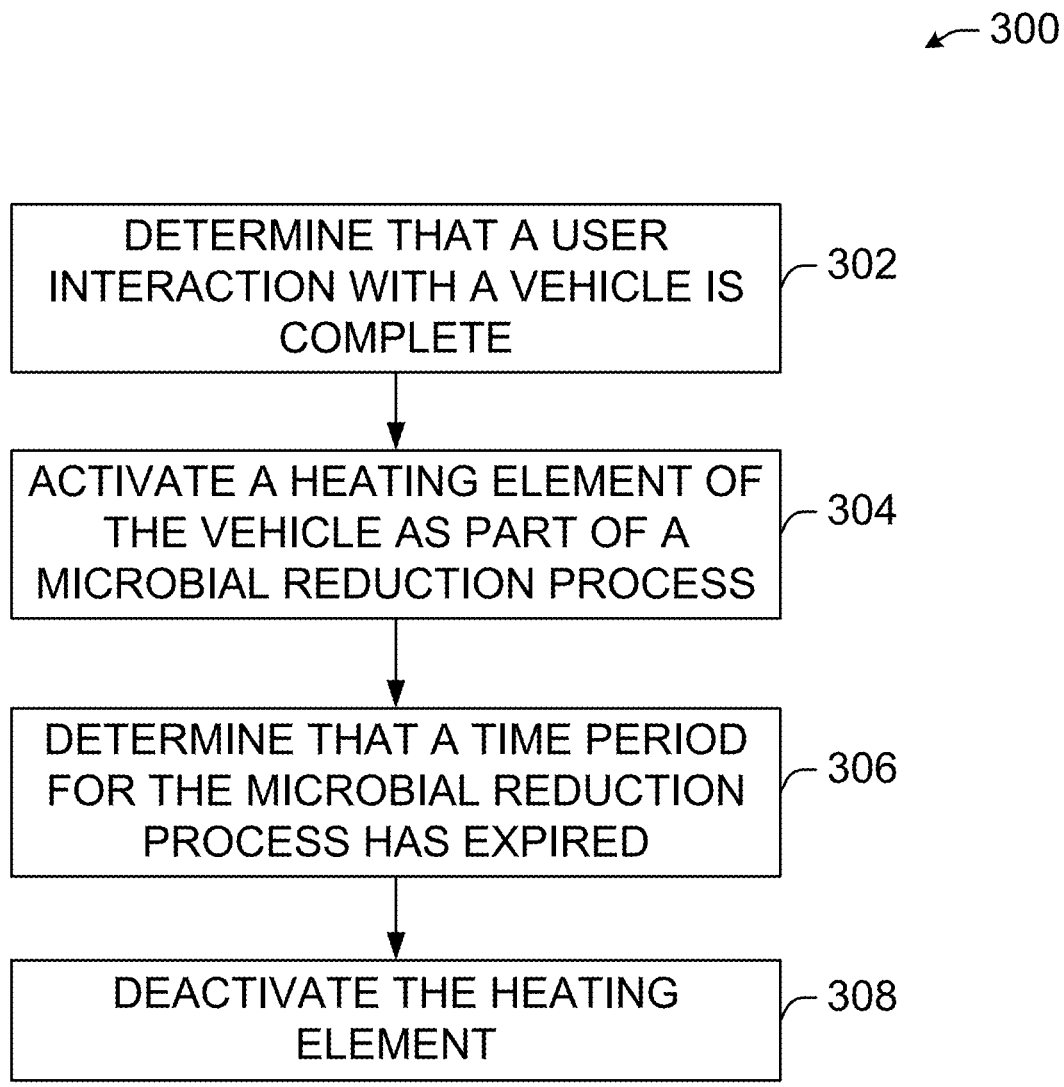
FIG. 3 is a flowchart of an example method for controlling microbial contamination on scooters.

FIG. 3 is a flowchart of an example method 300 for controlling microbial contamination on scooters.

At block 302, a vehicle device (or system, e.g., the transportation device 102 of FIG. 1) may determine that a user interaction with the vehicle is complete. The vehicle device may receive one or more notifications from another device (e.g., the mobile device 108 of FIG. 1) indicating that a user has completed use of the vehicle device. In addition or alternatively, the vehicle device may determine based on sensor data (e.g., from the one or more sensors 206 of FIG. 2) that a person is not in contact with the vehicle (e.g., not holding the handlebars 110 and/or the brake lever 160 of FIG. 1).

At block 304, the vehicle device may activate a heating element (e.g., the heating elements 150 of FIG. 1) associated with a microbial reduction process (e.g., a decontamination process) for the vehicle. Activation may include providing power to the heating element for a period of time related to the temperature of the heating element during the microbial reduction process. The microbial reduction process may include applying heat to handlebars and/or a brake lever of the vehicle by providing power to the heating element, resulting in the conduction of electricity. For example, the heating elements may operate at 56 degrees Celsius or greater for more than fifteen minutes to decontaminate the handlebars and/or the brake lever.

At block 306, the vehicle device may determine that a time period for the microbial reduction process has expired (e.g., that the heating element has operated at a temperature for the time period). For example, the time period may be greater than ten minutes. The vehicle may be unavailable for user during the time period (e.g., because the handlebars and/or the brake lever may be hot). In this manner, by ensuring that no one is using the vehicle before activating the heating elements, and may ensure that the heating elements and their surrounding materials are not too hot for a user before allowing the vehicle to be used by another rider.

At block 308, the vehicle device may deactivate the heating element (e.g., reduce the power supply to the heating element). Deactivation may result in the temperature of the handlebars and/or brake lever dissipating to below a temperature threshold (e.g., to be safe and comfortable enough for a person to touch). Once the temperature has dissipated to below the temperature threshold, the vehicle again may be available for use by another rider.

Figure 4:
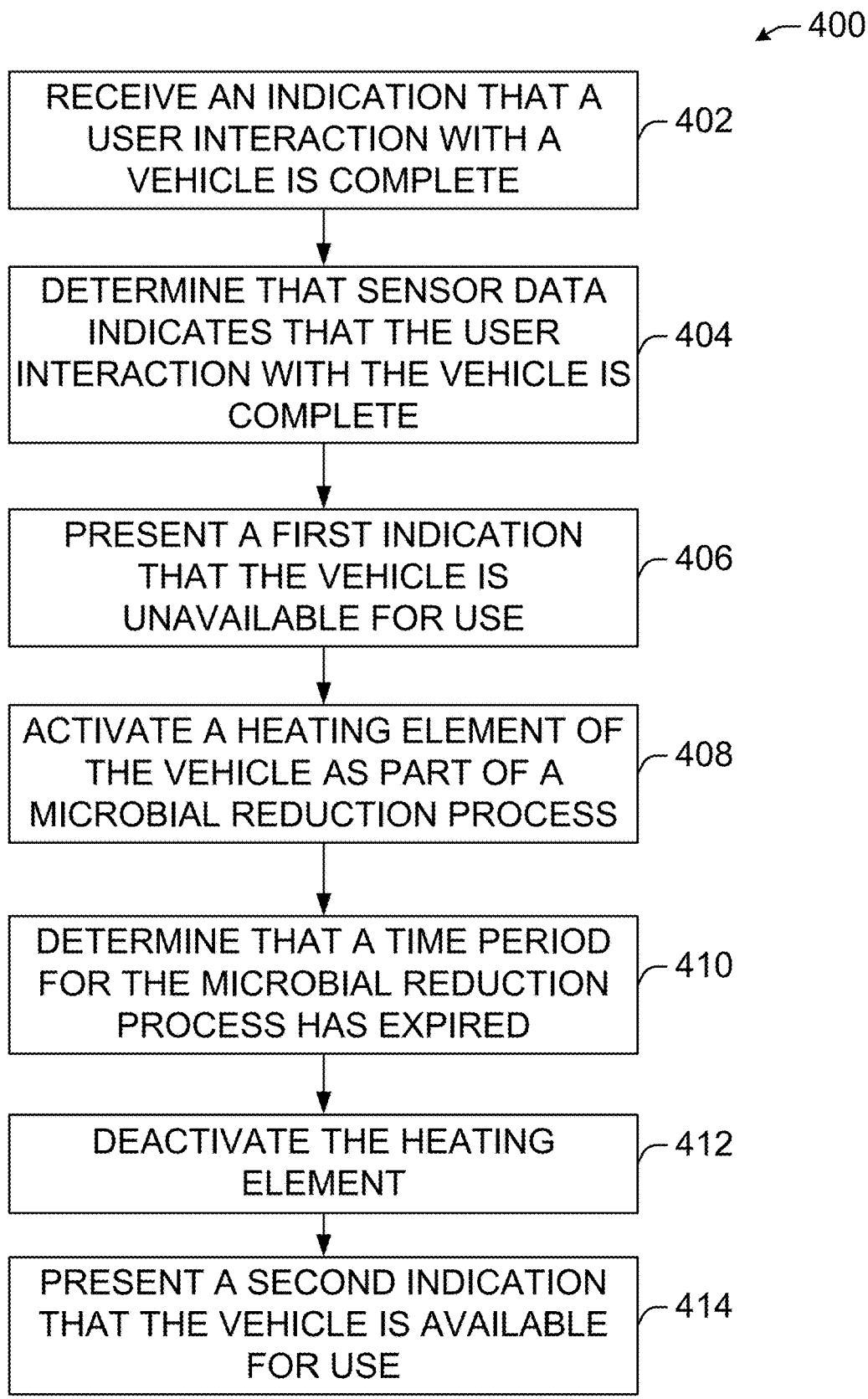
FIG. 4 is a flowchart of another method for controlling microbial contamination on scooters.

FIG. 4 is a flowchart of another method 400 for controlling microbial contamination on scooters.

At block 402, a vehicle device (or system, e.g., the transportation device 102 of FIG. 1) may receive an indication that a user interaction with the vehicle is complete. The vehicle may be reserved using a mobile application, for example, and once a reserved session for a rider is complete, the vehicle device may receive (e.g., from the mobile device 108 of FIG. 1) that the user is no longer using the vehicle.

At block 404, the vehicle device may determine that sensor data (e.g., from the one or more sensors 260 of FIG. 2) indicates that the user interaction is complete. For example, even after a device notification that a user's ride session with the vehicle is complete, the vehicle device may ensure that no one is using the vehicle by using temperature and/or pressure data (e.g., the sensor data) to determine whether a person may be touching the handlebars or brake lever of the vehicle. When a temperature and/or pressure of the handlebars and/or brake level exceed a threshold temperature or pressure, respectively, the vehicle device may determine that a person is touching the handlebars and/or brake level. When a temperature and/or pressure of the handlebars and/or brake level do not exceed the threshold temperature or pressure, respectively, the vehicle device may determine that a person is not touching the handlebars and/or brake level, and therefore that the vehicle is not in use.

At block 406, the vehicle device may present or cause presentation of a first indication that the vehicle is unavailable for use. For example, the handlebars may include a display (e.g., the display 210) capable of presenting messages indicating that the vehicle is available, unavailable, hot, in decontamination, etc. Alternatively or in addition, the vehicle may send messages to another device (e.g., the mobile device 108 of FIG. 1) to present indications of the vehicle's availability.

At block 408, the vehicle device may activate a heating element (e.g., the heating elements 150 of FIG. 1) associated with a microbial reduction process (e.g., a decontamination process) for the vehicle. Activation may include providing power to the heating element for a period of time related to the temperature of the heating element during the microbial reduction process. The microbial reduction process may include applying heat to handlebars and/or a brake lever of the vehicle by providing power to the heating element, resulting in the conduction of electricity. For example, the heating elements may operate at 56 degrees Celsius or greater for more than fifteen minutes to decontaminate the handlebars and/or the brake lever.

At block 410, the vehicle device may determine that a time period for the microbial reduction process has expired (e.g., that the heating element has operated at a temperature for the time period). For example, the time period may be greater than fifteen minutes. The vehicle may be unavailable for user during the time period (e.g., because the handlebars and/or the brake lever may be hot). In this manner, by ensuring that no one is using the vehicle before activating the heating elements, and may ensure that the heating elements and their surrounding materials are not too hot for a user before allowing the vehicle to be used by another rider.

At block 412, the vehicle device may deactivate the heating element (e.g., reduce the power supply to the heating element). Deactivation may result in the temperature of the handlebars and/or brake lever dissipating to below a temperature threshold (e.g., to be safe and comfortable enough for a person to touch). Once the temperature has dissipated to below the temperature threshold, the vehicle again may be available for use by another rider.

At block 414, the vehicle device may present or cause presentation of a second indication that the vehicle is available for use. For example, the handlebars may include a display (e.g., the display 210) capable of presenting messages indicating that the vehicle is available, unavailable, hot, in decontamination, etc. Alternatively or in addition, the vehicle may send messages to another device (e.g., the mobile device 108 of FIG. 1) to present indications of the vehicle's availability.

FIG. 5 is a block diagram illustrating an example of a computing device or computer system upon which any of one or more techniques (e.g., methods) may be performed, in accordance with one or more example embodiments of the present disclosure.

For example, the computing system 500 of FIG. 5 may include or represent the heating elements 150 of FIG. 1 and/or the one or more sensors 206 of FIG. 2, and therefore may allow for the determining of whether the mobile transportation device of 102 is in use or may activate a decontamination process. The computer system (system) includes one or more processors 502-506. Processors 502-506 may include one or more internal levels of cache (not shown) and a bus controller (e.g., bus controller 522) or bus interface (e.g., I/O interface 520) unit to direct interaction with the processor bus 512. The heating elements 150 and the sensors 206 may also be in communication with the Processors 502-506 and may be connected to the processor bus 512.

Processor bus 512, also known as the host bus or the front side bus, may be used to couple the processors 502-506, the heating elements 150, and/or the sensors 206 with the system interface 524. System interface 524 may be connected to the processor bus 512 to interface other components of the system 500 with the processor bus 512. For example, system interface 524 may include a memory controller 518 for interfacing a main memory 516 with the processor bus 512. The main memory 516 typically includes one or more memory cards and a control circuit (not shown). System interface 524 may also include an input/output (I/O) interface 520 to interface one or more I/O bridges 525 or I/O devices 530 with the processor bus 512. One or more I/O controllers and/or I/O devices may be connected with the I/O bus 526, such as I/O controller 528 and I/O device 530, as illustrated.

I/O device 530 may also include an input device (not shown), such as an alphanumeric input device, including alphanumeric and other keys for communicating information and/or command selections to the processors 502-506, the heating elements 150, and/or the sensors 206. Another type of user input device includes cursor control, such as a mouse, a trackball, or cursor direction keys for communicating direction information and command selections to the processors 502-506, and for controlling cursor movement on the display device.

System 500 may include a dynamic storage device, referred to as main memory 516, or a random access memory (RAM) or other computer-readable devices coupled to the processor bus 512 for storing information and instructions to be executed by the processors 502-506 and/or the heating elements 150. Main memory 516 also may be used for storing temporary variables or other intermediate information during execution of instructions by the processors 502-506 and/or the heating elements 150. System 500 may include read-only memory (ROM) and/or other static storage device coupled to the processor bus 512 for storing static information and instructions for the processors 502-506 and/or the heating elements 150. The system outlined in FIG. 5 is but one possible example of a computer system that may employ or be configured in accordance with aspects of the present disclosure.

According to one embodiment, the above techniques may be performed by computer system 500 in response to processor 504 executing one or more sequences of one or more instructions contained in main memory 516. These instructions may be read into main memory 516 from another machine-readable medium, such as a storage device. Execution of the sequences of instructions contained in main memory 516 may cause processors 502-506 and/or the heating elements 150 to perform the process steps described herein. In alternative embodiments, circuitry may be used in place of or in combination with the software instructions. Thus, embodiments of the present disclosure may include both hardware and software components.

According to one embodiment, the processors 502-506 may represent machine learning models. For example, the processors 502-506 may allow for neural networking and/or other machine learning techniques used to operate the personal transportation device 102.

In one or more embodiments, the computer system 500 may perform any of the steps of the processes described with respect to FIG. 3 and FIG. 4. For example, the computer system 500 may use sensor data from the sensors 206 and/or any notifications received (e.g., from the mobile device 108 of FIG. 1) to determine whether the personal transportation device 102 is in use or not. When the personal transportation device 102 is in use, the computer system 500 may prevent activation of the decontamination process. When the personal transportation device 102 is not in use, the computer system 500 may facilitate activation of the decontamination process by allowing for power to be provided (e.g., from the batteries 134 of FIG. 1) to the heating elements 150 for a period of time for the decontamination process. When the decontamination process is complete (e.g., after expiration of a time period), the computer system 500 may prevent the providing of power to the heating elements 150 and may wait until the temperature of the heating elements 150 have dropped to below a temperature threshold before allowing the personal transportation device 102 to be available.

Various embodiments may be implemented fully or partially in software and/or firmware. This software and/or firmware may take the form of instructions contained in or on a non-transitory computer-readable storage medium. Those instructions may then be read and executed by one or more processors to enable the performance of the operations described herein. The instructions may be in any suitable form, such as, but not limited to, source code, compiled code, interpreted code, executable code, static code, dynamic code, and the like. Such a computer-readable medium may include any tangible non-transitory medium for storing information in a form readable by one or more computers, such as but not limited to read-only memory (ROM); random access memory (RAM); magnetic disk storage media; optical storage media; a flash memory, etc.

A machine-readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, solid state devices (SSDs), and the like. The one or more memory devices (not shown) may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in main memory 516, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps.

Alternatively, the steps may be performed by a combination of hardware, software, and/or firmware.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations together with all equivalents thereof.

The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

The word "exemplary" is used herein to mean "serving as an example, instance, or illustration." Any embodiment described herein as "exemplary" is not necessarily to be construed as preferred or advantageous over other embodiments.

As used herein, unless otherwise specified, the use of the ordinal adjectives "first," "second," "third," etc., to describe a common object, merely indicates that different instances of like objects are being referred to and are not intended to imply that the objects so described must be in a given sequence, either temporally, spatially, in ranking, or any other manner.

It is understood that the above descriptions are for purposes of illustration and are not meant to be limiting.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A method, comprising:
    determining, by at least one processor of a vehicle, that a user interaction with the vehicle is complete;
    presenting, by the at least one processor, a first indication that the vehicle is unavailable for use;
    activating, by the at least one processor, a heating element of the vehicle, the heating element associated with a microbial reduction process;
    determining, by the at least one processor, that a time period associated with the microbial reduction process has expired;
    deactivating, by the at least one processor, based on expiration of the time period, the heating element of the vehicle; and
    presenting, by the at least one processor, a second indication that the vehicle is available for use.

2. The method according to claim 1, wherein the vehicle is a scooter.

3. The method according to claim 1, wherein the heating element is associated with a handlebar of the vehicle.

4. The method according to claim 1, wherein the heating element is associated with a brake lever of the vehicle.

5. The method according to claim 1, wherein the vehicle comprises a battery in a steering column of the vehicle, wherein activating the heating element is based on power supplied to the heating element by the battery.

6. The method according to claim 1, further comprising:
    receiving a request to initiate the user interaction; and
    receiving a request to end the user interaction, wherein determining that the user interaction with the vehicle is complete is based on the request to end the user interaction.

7. The method according to claim 1, wherein the first indication comprises a message indicative of the microbial reduction process.

8. A vehicle, comprising:
    a processor; and
    a memory for storing instructions, the processor executing the instructions to:
        determine that a user interaction with the vehicle is complete;
        present a first indication that the vehicle is unavailable for use;
        activate a heating element of the vehicle, the heating element associated with a microbial reduction process;
        determine that a time period associated with the microbial reduction process has expired;
        deactivate, based on expiration of the time period, the heating element of the vehicle; and
        present a second indication that the vehicle is available for use.

9. The vehicle according to claim 8, wherein the vehicle is a scooter.

10. The vehicle according to claim 8, wherein the heating element is associated with a handlebar of the vehicle.

11. The vehicle according to claim 8, wherein the heating element is associated with a brake lever of the vehicle.

12. The vehicle according to claim 8, wherein the vehicle comprises a battery in a steering column of the vehicle, wherein to activate the heating element is based on power supplied to the heating element by the battery.

13. The vehicle according to claim 8, wherein the processor is further configured to execute instructions to:
   receive a request to initiate the user interaction; and
   receive a request to end the user interaction, wherein to determine that the user interaction with the vehicle is complete is based on the request to end the user interaction.

14. The vehicle according to claim 8, wherein the first indication comprises a message indicative of the microbial reduction process.

15. A vehicle system, comprising:
   a vehicle;
   a user device;
   a processor; and
   a memory for storing instructions, the processor executing the instructions to:
      receive, from the user device, a first indication that a user interaction with the vehicle is complete;
      present a second indication that the vehicle is unavailable for use;
      activate a heating element of the vehicle, the heating element associated with a microbial reduction process;
      determine that a time period associated with the microbial reduction process has expired;
      deactivate, based on expiration of the time period, the heating element of the vehicle; and
      present a third indication that the vehicle is available for use.

16. The vehicle system according to claim 15, wherein the heating element is associated with a handlebar of the vehicle.

17. The vehicle system according to claim 15, wherein the heating element is associated with a brake lever of the vehicle.

18. The vehicle system according to claim 15, wherein the vehicle comprises a battery in a steering column of the vehicle, wherein to activate the heating element is based on power supplied to the heating element by the battery.

19. The vehicle system according to claim 15, wherein the processor is further configured to execute instructions to send, to the user device for presentation, a fourth indication that the vehicle is unavailable for use.

20. The vehicle system according to claim 15, wherein the processor is further configured to execute instructions to:
   receive a request to initiate the user interaction; and
   receive a request to end the user interaction, wherein to determine that the user interaction with the vehicle is complete is based on the request to end the user interaction.

* * * * *